United States Patent [19]

Hoffmann et al.

[11] 4,163,785

[45] Aug. 7, 1979

[54] BENZOTHIAZEPINE COMPOUNDS AND COMPOSITIONS

[75] Inventors: Charles Hoffmann, Fourqueux; Etienne Bouley, Franconville, both of France

[73] Assignee: Hexachimie, Malmaison, France

[21] Appl. No.: 892,647

[22] Filed: Apr. 3, 1978

[30] Foreign Application Priority Data

Apr. 7, 1978 [GB] United Kingdom ............... 14692/78

[51] Int. Cl.$^2$ .................. A61K 31/495; C07D 513/14
[52] U.S. Cl. ................................ 424/250; 260/243.3; 544/361
[58] Field of Search .................. 544/361; 424/250; 260/243.3

[56] References Cited

U.S. PATENT DOCUMENTS 3,412,193  11/1968  Coppola ............................ 424/250

FOREIGN PATENT DOCUMENTS 5315  4/1966  France.

1173826  12/1969  United Kingdom ................ 544/361

*Primary Examiner*—Donald G. Daus
*Assistant Examiner*—Lisa Jones
*Attorney, Agent, or Firm*—Bacon & Thomas

[57] ABSTRACT

The invention relates to 5-piperazinyl pyrido-[2,3-b][1,5] benzothiazepines of Formula I (I)

in which R is a hydrogen atom or a $C_{1-5}$ alkyl group and their non-toxic acid addition salts. These compounds have antihistamine and antianaphylaxic activity. The invention also relates to a method of preparing these compounds.

3 Claims, No Drawings

BENZOTHIAZEPINE COMPOUNDS AND COMPOSITIONS

The present invention relates to new derivatives of pyrido[2,3-b][1,5]benzothiazepine substituted at the 5-position by a piperazinyl radical and corresponding to the following formula:

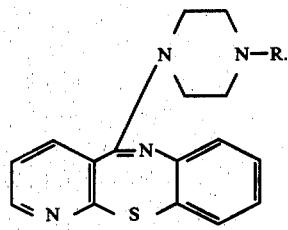
(I)

as well as to their non-toxic acid addition salts. The invention also relates to a method for the preparation of said new products and to the pharmaceutical use of said products.

In formula (I) R is a hydrogen atom or lower alkyl radical having 1 to 5 carbon atoms, with a straight or branched chain, preferably the methyl radical.

The invention also relates to a method for preparing the said compounds, according to which a piperazine of formula:

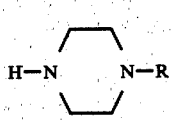
(II)

in which R is as above-defined, is reacted with a 5-halogenopyrido[2,3-b][1,5]benzothiazepine of formula III:

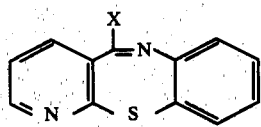
(III)

in which X is a halogen atom, preferably chlorine.

The reaction is preferably carried out in an aromatic solvent (advantageously toluene) at the boiling point of said solvent.

The compounds according to the invention have interesting pharmacological properties, in particular antihistamine and orexigenic actions, which make them therapeutically useful.

The following examples are given to illustrate the invention without limiting the scope of the latter.

EXAMPLE 1

5-Chloropyrido[2,3-b][1,5]benzothiazepine 40 g 5,6-dihydro-5-oxopyrido[2,3-b][1,5]benzothiazepine are added to a mixture of 200 cm$^3$ phosphorus oxychloride and 71 g phosphorus pentachloride. The reaction mixture is heated under reflux for 4 hours, then the excess phosphorus oxychloride is eliminated by distillation. The residue is then taken up in 300 cm$^3$ cold chloroform. The organic solution is washed several times with iced water, then dried over magnesium sulphate. The solvents are eliminated by distillation under vacuum at ambient temperature. The residue is taken up in anhydrous ether, then washed several times with cold ether. After drying under vacuum, 37 g 5-chloropyrido[2,3-b][1,5]benzothiazepine are obtained, having a melting point of 134°–135° C.

EXAMPLE 2

5-(1'-methyl-4'-piperazinyl)pyrido[2,3-b][1,5]benzothiazepine (Formula I, R=CH$_3$).

12.4 g 5-chloropyrido[2,3-b][1,5]benzothiazepine prepared in Example 1 are added at the same time to a solution of 10 g N-methyl piperazine in 75 cm$^3$ anhydrous toluene. The mixture is heated progressively to reflux, then this reflux is maintained for 2½ hours. The reaction mixture is poured into acidulated water and then left with stirring for half an hour. The aqueous phase is then washed with ether, made alkaline with ammonia to give a pH=8 and extracted with chloroform. The organic phase is dried over magnesium sulphate. After evaporation of the chloroform under vacuum, a pasty residue is obtained which precipitates from ether. This product (8 g) is re-crystallised from a mixture of 50 cm$^3$ acetone and 40 cm$^3$ water to give 5.7 g of the expected product having a melting point of 137° C.

The pharmacological properties of the products according to the invention are illustrated hereafter.

I-ANTIHISTAMINE ACTIVITY

Histamine bronchoconstrictor aerosol

Method

Batches of 6 guinea pigs weighing from 200 to 250 g are exposed to an aerosol of 0.2% histamine in an aqueous solution, in a small chamber for 5 minutes.

Two aerosols are used at an interval of 4 hours. The product tested is administered intraperitoneally 30 minutes before the use of the second aerosol.

Table I hereafter gives the percentage of animals protected who do not suffer an apneic crisis within 5 minutes.

TABLE I

| Product of Example 2 mg/kg intraperitoneally | % protection |
|---|---|
| 0.062 | 17 |
| 0.125 | 33 |
| 0.250 | 50 |
| 0.500 | 100 |
| ED$_{50}$ mg/kg intraperitoneally | 0.155 |

Action with regard to a LD$_{100}$ of histamine

Method

Male tricolour guinea pigs weighing 400 to 500 g receive the product studied intraperitoneally. 30 minutes later, 800 γ/kg histamine, or the LD 100 in physiological solution are injected intraveinously.

The animals are kept under observation for 1 hour.

Table II hereafter gives the percentage of protection with regard to mortality caused by histamine.

TABLE II

| Product of Example 2 mg/kg Intraperitoneally | % Protection |
|---|---|
| 0.062 | 0 |
| 0.125 | 60 |
| 0.250 | 100 |
| ED$_{50}$ mg/kg intraperitoneally | 0.120 |

II-OREXIGENIC ACTIVITY

Feeding of the cat

Method

Batches of 3 male cats weighing between 2 and 3 kg are conditioned to take their daily feed in one meal, between 10 and 12 a.m. Water is given ad libitum. The product to be tested is administered intraperitoneally, 30 minutes before the meal. The quantity of food absorbed is calculated.

With doses of 1 and 4 mg/kg (intraperitoneally) of the product of Example 2, the quantity of food absorbed has increased by 20 to 50% depending on the cats.

III ACTIVITY IN A PASSIVE CUTANEOUS ANAPHYLAXIS REACTION

Method

The method used is that described by MOTA I in "Immunology" 1964, 7, Page 681. This method consists of sensitizing rats by 4 intradermal injections of 0.1 ml rat antiserum. The antiserum is obtained from animals treated with a mixture of ovalbumin and bordetella pertussis. 72 hours after sensitization, the product to be studied and 1 ml per rat (IV) of a 0.25% solution of Evans blue+5 mg/ml ovalbumin in an isotonic aqueous solution of 9% sodium chloride are administered to the animals intravenously or intraperitoneally. Thirty minutes after this last injection, the animals are killed and one measures the surface area of each bruise corresponding to the point of injection of the antiserum.

The results are expressed as a percentage reduction of the coloured surface.

RESULTS

The results are given in Table III hereafter in which the results obtained with disodium cromoglycate (used intravenously) are also shown by way of comparison.

TABLE III

| Product | Method of administration | Doses mg/kg$^{-1}$ | Mean Surface area in mm$^2$ | % inhibition | T | ED$_{50}$ mg/kg$^{-1}$ |
|---|---|---|---|---|---|---|
| Ex. II | I.P. | 0 | 66.7 ± 2.62 | — | | |
| | | 0.125 | 54.4 ± 3.26 | 18 | ** | |
| | | 0 | 90.8 ± 5.92 | — | | |
| | | 0.5 | 46.3 ± 3.78 | 49 | *** | 0.57 |
| | | 0 | 66.7 ± 2.62 | — | | |
| | | 1 | 25.1 ± 3.45 | 62 | *** | |
| | | 0 | 31.77 ± 3.16 | — | | |
| | | 0.15 | 27.86 ± 3.82 | 12 | ns | |
| Disodium cromoglycate | IV | 0.31 | 30.5 ± 2.59 | 4 | ns | |
| | | 0 | 72.46 ± 4.37 | — | | 0.64 |
| | | 0.625 | 35.42 ± 5.02 | 51 | *** | |
| | | 0 | 31.77 ± 3.16 | — | | |
| | | 1.25 | 2.30 ± 1.07 | 93 | *** | |
| | | 2.5 | 0.23 ± 0.23 | 99 | *** | |

In conclusion, the compound of Example 2 has antihistamine, orexigenic and more particularly antianaphylaxic properties.

Said compound may thus be administered to humans in the case of inadequate weight, allergic and pruriginous disorders, as a preventive medicament for asthma in the form of capsules, syrup, tablets, injectable solutions or an aerosol. The therapeutic dose is approximately 1 to 15 mg active substance per day; the tablets and capsules will preferably contain a dose of 1 to 50 mg, the syrup will preferably contain a dose of 100 mg for 100 cm$^3$, the aerosol will preferably be dosed at the rate of 1 to 10 mg per inhalation and the injectable solution will preferably be dosed at the rate of 0.5 to 10 mg per ml.

What is claimed is:

1. A compound of the formula

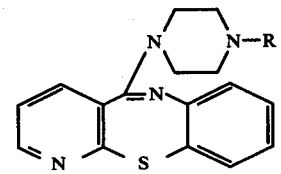

in which R is a hydrogen atom or alkyl of 1 to 5 carbon atoms, or a non-toxic acid addition salt thereof.

2. A compound according to claim 1, wherein R is a methyl radical.

3. A therapeutic composition having antihistaminic, orexigenic and antianaphylaxic activity, comprising an effective amount of a compound as claimed in claim 1 and a carrier therefor.

* * * * *